(12) United States Patent
Plouet et al.

(10) Patent No.: US 6,887,469 B2
(45) Date of Patent: May 3, 2005

(54) ANTI-IDIOTYPIC ANTIBODIES OF VASCULAR ENDOTHELIAL GROWTH FACTOR AND USE THEREOF AS DRUGS

(75) Inventors: Jean Plouet, Toulouse (FR); Frederic Jonca, Ramonville Saint Agne (FR); Nathalie Ortega, Toulouse (FR); Marie-Magdeleine Ruchoux, Tours (FR)

(73) Assignee: Centre National de la Recherche Scientifique, Paris (FR)

( * ) Notice: Subject to any disclaimer, the term of this patent is extended or adjusted under 35 U.S.C. 154(b) by 115 days.

(21) Appl. No.: 09/091,561

(22) PCT Filed: Dec. 20, 1996

(86) PCT No.: PCT/FR96/02041

§ 371 (c)(1),
(2), (4) Date: Aug. 21, 1998

(87) PCT Pub. No.: WO97/23510

PCT Pub. Date: Jul. 3, 1997

(65) Prior Publication Data

US 2002/0131966 A1 Sep. 19, 2002

(30) Foreign Application Priority Data

Dec. 21, 1995 (FR) .............................. 95 15243

(51) Int. Cl.$^7$ ........................................ A61K 39/395
(52) U.S. Cl. ................. 424/131.1; 424/278.1; 530/387.2; 530/388.1
(58) Field of Search .................... 424/131.1, 278.1; 530/387.2, 388.1

(56) References Cited

U.S. PATENT DOCUMENTS 4,737,453 A * 4/1988 Primus
4,792,447 A * 12/1988 Uhr et al.
5,942,385 A * 8/1999 Hirth .............................. 435/4

FOREIGN PATENT DOCUMENTS

EP 0 502 416 9/1992
WO WO 94/11499 5/1994

OTHER PUBLICATIONS

Kieber–Emmons et al. in Intern. Rev. Immun., Köhler ed. 1:1–26, 1986.*
Plouet et al., J. Cell Biochem. "VEGF Tumoral Progression: STLM By αVEGF Idiotypic AB." Supp. 18A, XP000602723, p. 328, AB EZ311, 1994.*
by Plouet et al., "VEGF Dependent Tumoral Progression: Stimulation by Anti VEGF Idiotypic Antibodies", *Journal of Cellular Biochemistry*, Supplement 18A, 1994, p. 328.
by Terman et al., "Identification of the KDR Tyrosine Kinase as a Receptor for Vascular Endothelial Cell Growth Factor", *Biochemical and Biophysical Research Communications*, vol. 187, No. 3, 1992, pp. 1579–1586.
by Millauer et al., "High Affinity VEGF Binding and Developmental Expression Suggest Flk–1 as a Major Regulator of Vasculogenesis and Angiogenesis", *Cell*, vol. 72, 1993, pp. 835–846.
by Millauer et al., "Glioblastoma Growth Inhibited in vivo by a Dominant–Negative Flk–1 Mutant", *Nature*, vol. 367, 1994, pp. 576–579.
by Kim et al., "Inhibition of Vascular Endothelial Growth Factor–Induced Angiogenesis Suppresses Tumour Growth in vivo", *Nature*, vol. 362, 1993, pp. 841–844.
by Chagnaud et al., "Curative Effects on Rat Sarcomas Obtained After a Treatment Combining Two Monoclonal Antibodies", *Anti–Cancer Drugs*, vol. 5, 1994, pp. 361–366.

* cited by examiner

*Primary Examiner*—G. R. Ewoldt
(74) *Attorney, Agent, or Firm*—Young & Thompson (57) ABSTRACT

An anti-idiotypic vascular endothelial growth factor antibody, an Fab fragment, and pharmaceutical compositions thereof, being ligands of the human KDR receptor or of the murine flk-1 receptor and not a ligand of flt are provided.

10 Claims, 7 Drawing Sheets

ANTI-IDIOTYPIC ANTIBODIES OF VASCULAR ENDOTHELIAL GROWTH FACTOR AND USE THEREOF AS DRUGS

This application is a 371 national stage application of PCT/FR96/02041, filed Dec. 12, 1996, which claims the benefit of priority to French Appln. No. 95.15423, filed Dec. 21, 1995.

The invention relates to anti-idiotypic vascular endothelial growth factor antibodies and their use as medicaments.

VEGF (vascular endothelial growth factor) is currently recognized as the main agent of uncontrolled neovascularization observed in tumour progression (review in Folkman), diabetic retinopathy (Malecaze, 1994) or rheumatoid polyarthritis (Fava, 1994). It is a glycoprotein of 46 kDa which binds to heparin (Plouët Ferrar Connolly). At least 3 homodimeric forms of 121, 165 and 189 amino acids are generated by alternative splicing of premessenger RNA. The VEGF of 165 amino acids will be called VEGF 165. In addition to its angiogenic role, VEGF stimulates capillary permeability (Connolly, 1989). The role of VEGF in tumorigenesis has been suspected from the observation that the hypoxia which accompanies tumour necrosis increased the expression of its mRNAs. On the other hand, VEGF is over-expressed in many cases of tumour pathology. Furthermore, injection of anti-VEGF antibodies inhibits the growth of tumours (Kim, 1993).

A growth factor can thus induce many different effects, according to whether it binds to one or other of its receptors, for example proliferation and survival. Immunoneutralization can therefore have beneficial effects by inhibiting proliferation, but also undesirable effects by reducing survival. Analysis of the functions mediated in vivo by a receptor of a growth factor which binds to heparin, such as VEGF or FGFs (fibroblast growth factors) meets two major obstacles. On the one hand, the combination of interactions between ligands and receptors is highly complex, since a growth factor can bind to several receptors, and furthermore several growth factors can bind to the same receptor. The products of 9 genes which code for FGFs thus have available products of 5 genes which code for the receptors of the FGFs. On the other hand, their high affinity for glycosaminoglycans means that the growth factors such as VEGF or FGF are sequestrated in the extracellular matrices and are found only in the immediate vicinity (less than 0.5 mm) of their synthesis site, which makes it difficult to understand their role in vivo.

Two different genes code for the transmembrane tyrosine kinases identified as VEGF receptors: KDR in man (Terman, 1992) or flk-1 in the mouse (Millauer, 1993) and flt-1 (DeVries, 1992).

It has been demonstrated that the messenger RNAs of the flk-1 receptor were present in endothelial cells during embryogenesis and disappeared in the adult (Millauer, 1993). The only non-endothelial cells where flk-1 has been found are the stromal cells of the umbilical cord (Quinn, 1993). Other authors have demonstrated the presence of the mRNA of flk-1 in adult hepatic sinusoidal endothelial cells (Yamane, 1994), adult glomerules (Millauer, 1994) and β islets of Langerhans (Oberg, 1994).

Moreover, concomitant inoculation of tumour cells and cells infected by dominant negative flk-1 receptors inhibits tumour growth (Millauer, 1994).

One of the objects of the invention is to propose the use of anti-idiotypic antibodies of growth factors having a affinity for heparin, enabling to target specifically a new type of circulating agonists on one or other of their receptors.

One of the other aspects of the invention is to provide agonists of growth factor receptors which have a suitable specificity and a long half-life.

One of the other objects of the invention is to provide internal images of the binding regions of VEGF with KDR which, because of their immunoglobulin structure, are circulating.

The invention relates to anti-idiotypic vascular endothelial growth factor antibodies for the preparation of a medicament for treatment of pathologies involving endothelial cells engaged in an angiogenesis process, either to inhibit the angiogenesis or to promote the angiogenesis, without affecting quiescent endothelial cells, or for the preparation of a product for diagnosis of pathologies involving endothelial cells engaged in an angiogenesis process.

The expression "endothelial cells engaged in an angiogenesis process" means endothelial cells migrating through the basal lamina and multiplying.

To determine whether cells are engaged in an angiogenesis process, immunomarking with the aid of antibodies directed against the integrin β3 can be used (Brooks et al., Cell, 1994, 79:1157–1164).

The expression "quiescent endothelial cells" means endothelial cells of normal adult, non-angiogenic vessels.

The invention relates to the use of anti-idiotypic vascular endothelial growth factor antibodies for the preparation of a medicament for treatment of pathologies involving angiogenic endothelial cells by selective stimulation of the KDR receptor.

The expression "angiogenic endothelial cells" designates the cells involved in an angiogenesis process.

The anti-idiotypic antibodies of the invention recognize the human KDR receptor (or the murine flk-1 receptor), but do not recognize the flt-1 receptor.

With the aid of the anti-idiotypic antibodies of the invention, it has been possible to demonstrate the fact that KDR (or flk-1) is the target of pathological angiogenesis.

According to an advantageous embodiment, the invention relates to the use of anti-idiotypic vascular endothelial growth factor antibodies for the preparation of a medicament for treatment of pathologies involving endothelial cells engaged in an angiogenesis process, to inhibit the angiogenesis, without affecting the quiescent endothelial cells, which anti-idiotypic antibody is coupled with a toxin, the function of which is to block translation of proteins.

As the toxin there may be mentioned saporin, ricin or a radioactive element, such as iodine-125 or -131.

According to another advantageous embodiment, the invention relates to the use of anti-idiotypic vascular endothelial growth factor antibodies for the preparation of a medicament for treatment of pathologies involving endothelial cells engaged in an angiogenesis process, to inhibit the angiogenesis, without affecting the quiescent endothelial cells, which anti-idiotypic antibody is in the form of its Fab fragment.

As pathologies for treatment of which inhibition of angiogenesis is required there may be mentioned cancer, diabetic retinopathies and rejection of corneal grafts.

The invention relates to the use of anti-idiotypic vascular endothelial growth factor antibodies for the preparation of a medicament for treatment of pathologies involving endothelial cells engaged in an angiogenesis process, to promote the angiogenesis, without affecting quiescent endothelial cells.

As pathologies for treatment of which stimulation of angiogenesis is required there may be mentioned cicatrization and reperfusion of regions rendered ischaemic during arterial or venous thrombosis.

The invention relates to the use of anti-idiotypic antibodies for the preparation of a medicament for stimulation of physiological angiogenesis, to increase the speed of formation of blood vessels in the course of cicatrization or maturation of the corpus luteum of the ovary, or for stimulation of angiogenesis in the course of obstructive pathologies of vessels in order to reperfuse regions rendered ischaemic during vascular thrombosis.

The anti-idiotypic antibodies of the invention can also be used for the preparation of a product for diagnosis of pathologies involving endothelial cells engaged in an angiogenesis process.

The demonstration of the absence of a reaction of healthy tissue to KDR stimulation by a general route opens up the route to mapping regions which express KDR or flk-1. Injection of iodinated anti-idiotypic vascular endothelial growth factor antibodies can allow visualization of tumours without binding to healthy organs.

The invention relates to an anti-idiotypic vascular endothelial growth factor antibody, characterized in that it is a ligand of the human KDR receptor or of the murine flk-1 receptor and in that it is not a ligand of flt.

The invention relates to anti-idiotypic vascular endothelial growth factor antibodies, characterized in that they have the following properties:
they are specific to KDR,
they are circulating,
they have a half-life of about 23 days, especially about 21 days, and in particular 22.5 days,
they induce phosphorylation on a tyrosine of a protein of 200 kDa,
they induce proliferation of vascular endothelial cells,
they do not induce migration of endothelial cells,
they stimulate angiogenesis,
they do not cause arterial hypotension,
they do not affect the permeability of vessels.

The specificity for KDR can be determined by the competition test with radioiodinated VEGF with respect to its binding to COS cells transfected with eukaryotic expression vectors containing the KDR sequence (Terman et al., Biochem. Biophys. Res. Commun., 1992, 187:1579–1596).

In contrast to the anti-idiotypic antibodies of the invention, VEGF is not specific to KDR since it can bind to the flt receptor.

The advantage of the specificity of the anti-idiotypic antibodies of the invention lies in targeting angiogenic endothelial cells with drugs which do not affect quiescent endothelial cells.

The expression "circulating" means transported freely in the circulating blood and not caught on the vascular walls.

In contrast to the anti-idiotypic antibodies of the invention, VEGF is not circulating. The advantage of the anti-idiotypic antibodies of the invention being circulating lies in targeting angiogenic endothelial cells with drugs which do not affect quiescent endothelial cells.

As regards the half-life of the anti-idiotypic antibodies, this varies from one species to another; for example for the rat it is 7 days.

The half-life of the antibodies of the invention can be measured by the following test: Intravenous injection of 1 $\mu$Ci of radioiodinated ligand, and then collection of blood at various intervals of time and counting of the radioactivity. The half-life corresponds to the time required for 50% of the initial radioactivity to have disappeared from the circulating blood.

The half-life of VEGF is less than 6 minutes (Beuters et al., Circulation, 1995); the half-life of IgG is of the order of 23 days.

The protein of 200 kDa on which the anti-idiotypic antibodies induce phosphorylation of a tyrosine is KDR.

This aspect means that the activation of KDR by the anti-idiotypic antibodies can trigger off functions requiring phosphorylation of KDR.

This aspect can be measured by the phosphorylation test described in the examples.

Induction of the proliferation of vascular endothelial cells means that they multiply.

This can be determined by the test described in the examples.

The antibodies of the invention induce the proliferation of vascular endothelial cells more potently than VEGF, that is to say in a ratio of about 2-fold.

The advantage of this increase in the induction of the proliferation of endothelial cells by the anti-idiotypic antibodies of the invention lies in the fact that the binding of anti-idiotypic antibodies to the KDR receptor followed by phosphorylation on a tyrosine of the KDR is sufficient to trigger off cell proliferation.

The absence of migration of endothelial cells means that, among the effects triggered off by VEGF, the anti-idiotypic antibodies mimic those which are mediated by KDR and not those which are mediated by flt-1.

This aspect can be measured by the test described in the examples.

In contrast to the antibodies of the invention, VEGF induces migration of endothelial cells.

The advantage presented by the antibodies of the invention lies in demonstrating their absence of an effect on the flt-1 receptor by migration and permeability tests which explore the function of flt-1.

Stimulation of angiogenesis means that binding of the anti-idiotypic antibodies to the KDR receptor followed by phosphorylation on a tyrosine of KDR and cell proliferation is sufficient to trigger off angiogenesis.

This can be quantified by the test described in the examples.

The fact that the antibodies of the invention do no affect the permeability of vessels means that, among the effects triggered off by VEGF, the anti-idiotypic antibodies mimic those which are mediated by KDR and not those which are mediated by flt-1, for example vascular permeability.

This can be determined by the following test: Filter papers (12 mm diameter) which have been incubated beforehand for 16 hours at 4° C. with PBS supplemented with 2 mg/ml gelatine (Millicell-Millipore) are seeded with endothelial cells of the cornea (40,000 cells/cm$^2$). The wells are arranged in boxes of 24 wells (16 mm diameter). After 5 days, the electrical resistance between the intracellular and extracellular compartment is measured (of the order of 180 $\Omega$). The modulators are added and the resistance is measured every 10 minutes. Under the influence of VEGF (5–50 ng/ml), the resistance drops to 150 m in the course of about 90 minutes. A reduction in the resistance thus represents an increase in permeability. This function is mediated by the flt-1 receptor and not by the KDR receptor.

In contrast to the antibodies of the invention, VEGF affects the permeability of vessels. The advantage of the invention thus lies in demonstrating that the anti-idiotypic antibodies do not stimulate in vivo the effects mediated by the flt-1 receptor.

The invention also relates to the Fab fragment of the anti-idiotypic antibodies according to the invention.

The invention also relates to the complex between an anti-idiotypic antibody according to the invention and a toxin, in particular chosen from saporin and ricin, or between an anti-idiotypic antibody according to the invention and a radioactive element, such as iodine-125 or -131.

The invention also relates to an anti-idiotypic antibody according to the invention which can be obtained by the following process:

purified VEGF is injected into an animal, in particular a rabbit, blood is withdrawn to recover purified Ig containing specific anti-VEGF IgG, for example by affinity chromatography for protein A, and then in a possible stage the specific anti-VEGF IgG are purified from the purified Ig, for example by affinity chromatography for VEGF, the abovementioned purified Ig or the abovementioned purified anti-VEGF IgG are injected into an animal of the same species as that used for injection of the VEGF, in particular into the popliteal ganglions of a rabbit of the same origin as that used for injection of the VEGF, blood is withdrawn to recover the total Ig, for example by protein A, and then to subject the total Ig to two immunoadsorptions:

an immunoadsorption on an affinity column prepared with the pre-immune Ig of the rabbit which has been used to produce the anti-VEGF IgG, to eliminate the anti-allotypic or isotypic antibodies, an immunoadsorption on an affinity column prepared with the anti-VEGF IgG, to purify the anti-idiotypes.

To prove the in vivo action of the anti-idiotypes of the invention, merely purification on protein A-sepharose is necessary.

The invention also relates to a process for the preparation of an anti-idiotypic antibody according to the invention, characterized in that:

purified VEGF is injected into an animal, in particular a rabbit, blood is withdrawn to recover purified Ig containing specific anti-VEGF IgG, for example by affinity chromatography for protein A, and then in a possible stage the specific anti-VEGF IgG are purified from the purified Ig, for example by affinity chromatography for VEGF, the abovementioned purified Ig or the abovementioned purified anti-VEGF IgG are injected into an animal of the same species as that used for injection of the VEGF, in particular into the popliteal ganglions of a rabbit of the same origin as that used for injection of the VEGF, blood is withdrawn to recover the total Ig, for example by protein A, and then to subject the total Ig to two immunoadsorptions:

an immunoadsorption on an affinity column prepared with the pre-immune Ig of the rabbit which has been used to produce the anti-VEGF IgG, to eliminate the anti-allotypic or isotypic antibodies, an immunoadsorption on an affinity column prepared with the anti-VEGF IgG, to purify the anti-idiotypes.

To prepare the Fab fragment of the antibodies of the invention, the procedure can be as follows: The Fab fragments are prepared from 200 mg Ig2 Id dissolved in 42 ml containing 3.5 mg papain and 0.1 M EDTA (ethylenediaminetetraacetic acid) and 0.1 M cysteine. The mixture is incubated for 4 hours at 37° C. and the reaction is then stopped with 4.6 ml of 0.3 M iodoacetamide. The mixture is then dialysed against 2 liters of PBS at 4° C. for 16 hours and then chromatographed over a column of 10 ml protein A-sepharose. The Fab fragments are recovered in the dead volume.

The invention also relates to pharmaceutical compositions, characterized in that they comprise, as the active substance, at least one anti-idiotype according to the invention, or at least one Fab fragment according to the invention, or at least one complex according to the invention.

The invention also relates to pharmaceutical compositions derived from sequences of the hypervariable regions of the Fab fragments of the anti-idiotypic antibodies.

The invention also relates to pharmaceutical compositions derived from the three-dimensional structure of the Fab fragments of the anti-idiotypic antibodies determined by crystallography and X-ray diffraction, circular dichroism and nuclear magnetic resonance.

DESCRIPTION OF THE FIGURES

The concentrations of VEGF or anti-Id J indicated are incubated with COS cells transfected 48 hours beforehand with 1 $\mu$g/ml vector pSV7d containing the flt-1 sequence (part A of the figure) or flk-1 sequence (part B of the figure) in the presence of 1 ng/ml (part A of the figure) or 10 ng/ml (part B of the figure) of iodinated VEGF at 4 C. After 3 hours, the cells are rinsed and lysed and the radioactivity is counted in a gamma counter.

Subconfluent FBAE cells seeded in 12-well plates are transfected with 2 $\mu$M sense (□) or antisense (♦) KDR oligonucleotides. 24 hours later, the cells are incubated for three hours at 4° C. in the presence of increasing concentration of iodinated VEGF in a final volume of 500 $\mu$l.

Subconfluent FBAE cells are seeded in wells of 10 cm$^2$ and incubated, for internalization, with 5 $\mu$g/ml anti-Id J or pre-immune IgG at 37° C. for 90 min. The plates are then transferred to 4° C. and incubated with various concentrations of iodinated VEGF. The non-specific binding is determined in the presence of 1 $\mu$g/ml cold VEGF (inset). The data are then expressed by the Scatchard plot.

FBAE cells are stimulated for 10 min at 37° C. by pre-immune IgG, VEGF or anti-Id J, and are then lysed in RIPA buffer, and the lysate is immunoprecipitated with an anti-phosphotyrosine monoclonal antibody (PY22). The immunocomplexes are collected on protein A-sepharose beads, subjected to polyacrylamide gel electrophoresis, transferred to a nitrocellulose filter and revealed either by an anti-phosphotyrosine monoclonal antibody PY22 or by an anti-flk-1 polyclonal antibody.

FBAE cells are seeded at 5,000 cells per well in plates of 12 wells in the presence of VEGF, anti-Id J or pre-immune IgG at various concentrations ranging from 0.01 ng/ml to 1,000 ng/ml. After five days, the cells are trypsinized and counted. The data shown are the means of three points, and the experiments were carried out four times with similar results.

Fragments of hormone-independent prostate adenocarcinoma corresponding to a Gleason score of IX (3×3×3 mm)

were grafted into nu/nu female mice. One month later, when they become clinically palpable, the animals (n=8–10 for each group) receive 200 μg Ig1 T which neutralizes the activity of VEGF (V-IgG), or Ig1 PI (PI-IgG), or Ig2 Id (J-IgG) twice a week. The tumour volume was measured twice a week with the aid of slide callipers and the mice were weighed. The animals were sacrificed 3 months later and the tumours were photographed.

The animals treated as indicated in the legend of FIG. 5 were sacrificed 3 months after implantation of the xenografts, and sections are then made in these tumours and stained with haematoxylin-eosin (a–c). Adjacent sections were revealed with ulex marker (d–f) (Ulex Europeaus conjugated with peroxidase, Sigma, ref. L8146), anti-flt-1 antibody (Santa Cruz) (g–i) or mib-1 (j–l).

TABLE 1

| | PROLIFERATION (incorporation of $^3$HTDR cpm/well) | | MIGRATION (cells/field) | |
|---|---|---|---|---|
| | Sense | Antisense | Sense | Antisense |
| none | 30,604 ± 4,820 | 32,645 ± 4,820 | 36.4 ± 5.5 | 27.2 ± 5.2 |
| VEGF | 75,098 ± 4,511 | 46,223 ± 2,104 | 74.0 ± 6.1 | 81.2 ± 8.1 |
| Anti-Id J | 104,355 ± 6,212 | 35,462 ± 3,874 | 31.2 ± 2.1 | 33.4 ± 5.4 |

Table 1 shows the biological effects of VEGF and anti-Id J on FBAE cells transfected by sense or antisense KDR oligonucleotides.

Subconfluent FBAE cells are transfected by sense or antisense KDR oligonucleotides as described in the above description. Twenty-four hours later, the cells are transferred to medium without serum, they are subsequently incubated in the presence of 50 pM VEGF, anti-Id J or neither, and are then marked for 4 hours with tritiated thymidine after stimulation for 20 hours. In parallel, migration experiments are carried out on confluent cells. An incision in the form of a Maltese cross is made on the monolayer of cells. The wells are washed with medium without serum and the cells are incubated with modulator concentrations which are ten times higher. Twenty-four hours later, the cells are stained with May-Grunwald-Giemsa stain and the cells which have migrated are counted over eight fields, each point being determined in triplicate. These experiments were carried out three times with similar results.

Abbreviations Used in the Example

PBS (phosphate-buffered saline): saline solution of phosphate buffer.

Ig1 PI: rabbit immunoglobulins purified by protein A-sepharose from blood withdrawn before immunization with VEGF.

Ig1 T: rabbit immunoglobulins purified by protein A-sepharose from blood withdrawn after immunization with VEGF.

anti-VEGF Ig1: Ig1 T purified by VEGF-sepharose.

Ig2 Id: rabbit 2 immunoglobulins purified by protein A-sepharose from blood withdrawn after immunization with Ig1 T. Ig2 J: Ig2 Id purified by Ig1 PI-sepharose and then anti-VEGF Ig1-sepharose.

STUDY METHODS

Example
1. Production of Anti-Idiotypic VEGF 165 Antibodies
   Preparation of the Pre-Immune IgG (Ig1 PI):

Before each immunization, blood is withdrawn, the serum is fractionated immediately after collection, and 15 ml serum are chromatographed over a column of protein A (0.9×18 cm). The column is washed with PBS and the immunoglobulins are eluted with 0.2 M glycine buffered at pH 2.5, neutralized immediately by addition of ⅕ of the volume of 1 M $K_2HPO_4$ and then dialysed against PBS. The immunoglobulins (Ig1 PI) are stored at 80° C. until used.

1.1. Preparation of Murine Anti-Idiotypic Antibodies

AtT20 cells cultured to confluence and then transferred into DMEM medium (Dulbecco's Modified Eagle Medium (Gibco, ref. 13016 027) containing 5 μg/ml insulin and 10 μg/ml transferrin are stimulated by 5 ng/ml recombinant FGF2 produced in *Escherichia coli* (donated by Dr. Hervé Prats, U397 INSERM, Toulouse) for 48 hours to increase the production of VEGF (Plouët, 1992).

The conditioned medium (30 liters) was purified as described above (Plouët, 1989). Forty μg murine VEGF are separated by polyacrylamide gel electrophoresis under denaturing conditions and transferred to a nitrocellulose leaf.

The fraction containing the VEGF was cut out and then dissolved in 1 ml dimethylsulphoxide. Ten μg VEGF are emulsified in 0.25 ml Freund's complete adjuvant and then injected into a "Fauve de Bourgogne" rabbit (Iffa-Credo) 4 times at intervals of 15 days.

The blood withdrawn between 3 and 7 months after the first injection is fractionated and the Ig are purified by affinity chromatography for protein A; these purified Ig are called Ig1 T.

Anaesthetized "Fauve de Bourgogne" rabbits receive an injection of 0.5 ml PBS containing Evans blue in the paw pad in order to stain the lymphatic system. A cutaneous incision is then made, the cutaneous levels freed, and the ganglion which has become blue is thus visualized.

Ten μg Ig1 T (5 μl) emulsified in 100 μl of a 1:1 mixture of PBS/Freund's complete adjuvant are injected into the popliteal ganglion of each of the rabbits 30 minutes later.

Injection of the adjuvant creates an inflammatory granuloma, which enables the ganglion to be felt and therefore transcutaneous injection subsequently to be carried out without an incision of the cutaneous level being necessary. 3, 6 and 9 weeks later, the rabbits receive an intra-ganglionic injection of 10 μg Ig1 T.

The blood withdrawn between 4 and 7 months after the first injection is purified as described above. The anti-idiotypic Ig (lg2 J) are then purified by a series of 2 affinity chromatographies as indicated in paragraphs 2 and 3 below.

1.2. Preparation of Human Anti-Idiotypic Antibodies

VEGF 165 was produced in CHO cells transfected in a stable manner by an expression plasmid (prCEN-1, F. Bayard, Unit 397 INSERM) containing the cDNA of VEGF 165 (donated by Judith Abraham, Scios Nova, Mountain View, Calif.).

The cells are cultured to confluence in DMEM medium containing antibiotics and 10% new-born calf serum, and then rinsed 3 times with DMEM medium without serum and incubated for 48 hours in DMEM medium containing 5 μg/ml insulin and 10 μg/ml transferrin.

Two days later, the medium is collected, centrifuged (20,000 g, 30 minutes) and then chromatographed over heparin-sepharose (0.9×6 cm) equilibrated beforehand in 0.01 M Tris buffer, pH 7.2, containing 0.05 M NaCl. After the column has been washed in the same buffer, the VEGF is eluted by a concentration gradient of NaCl in Tris buffer. The biological activity of the VEGF is measured by its mitogenic activity (Plouët, 1989). The media are then centrifuged and the amount of VEGF produced is quantified by radioreceptor assay and by measuring the competition with iodinated VEGF with respect to binding to its receptors.

Ten µg VEGF are injected into the popliteal ganglions of a New Zealand rabbit (INRA, Toulouse) as described above. After 3–7 months, the Ig1 T are examined for their capacity to neutralize the mitogenic effect of VEGF on ACE cells (endothelial cells of the capillaries of the bovine adrenocortex).

Co-isogenic rabbits receive injections of 10 µg Ig1 T in accordance with the protocol described above.

2-Construction of the Immunoadsorbents

VEGF-Sepharose

One g sepharose-CNBr (Pharmacia) is kept in contact with 2 mg VEGF, dialysed beforehand against 0.1 M carbonate buffer, pH 8.5, for one night. After this time, the matrix is washed by centrifugation (2,000 g, 5 minutes) 3 times with 10 ml carbonate buffer. The amine functions which are still free are then blocked by incubation with 5 ml 0.2 M ethanolamine. The matrix is washed again 3 times with PBS, once with 0.2 M glycine, pH 2.5, for 5 minutes, and then with 10 ml $K_2HPO_4$. The matrix is then stored in PBS, supplemented with 0.02% sodium azide, until used.

Pre-immune Ig1

The affinity matrix is prepared as above, bringing 1 g CNBr-sepharose and 5 mg Ig1 PI into contact.

Anti-VEGF Ig1

Fifty mg Ig1 T are chromatographed over the sepharose-VEGF column, eluted with 0.2 M glycine, pH 2.5, dialysed and frozen at −80° C until used. The VEGF-specific Ig represent 8% of the Ig1 T.

3-Purification of the Anti-Idiotypic Ig

The anti-idiotypic Ig purified over protein A-sepharose (Ig2 Id) are purified by a sequence of 2 affinity chromatographies: chromatography over Ig1 PI-sepharose and chromatography over anti-VEGF Ig1-sepharose.

Ig1 PI-Sepharose

Fifty mg Ig2 Id are inoculated on to the Ig1 PI-sepharose column arranged in an Economo-pack column (0.2×1 cm). Once the Ig2 have been separated from any Ig2 Id directed against the isotypes and allotypes of Ig1 PI, therefore bound to the Ig1 PI-sepharose, the fraction which is not retained, therefore composed of non-immune regular Ig and the Ig2 J directed against the Ig1 regions which recognize VEGF, is deposited on an anti-VEGF Ig1-sepharose column.

It has never been found that this procedure enables a measurable amount of anti-isotypic and anti-allotypic Ig to be separated.

Anti-VEGF Ig1-Sepharose

The anti-id Ig which are not retained on the Ig1 PI column, therefore depleted of any anti-isotypic and anti-allotypic antibodies, are inoculated on to the VEGF Ig1-sepharose column arranged in an Economo-pack column (0.2×1 cm).

The column is subsequently washed with 10 ml PBS, and the Ig retained are then eluted with 0.2 M glycine, pH 2.5, neutralized immediately with one fifth of the volume of 1 M $K_2HPO_4$ and then dialysed against PBS.

This procedure enables the anti-idiotypic immunoglobulins (Ig2 J), which represent 2–3% of the total Ig2 Id, to be purified.

4. Study of the Specificity of the Antibodies

Screening of the anti-idiotypic antibodies is carried out in accordance with the following sequence developed in the laboratory:

COS cells seeded at 30,000 cells per well of 2 cm² are cultured in DMEM medium containing 10% foetal calf serum, 100 IU/ml penicillin and 50 µg/ml streptomycin. Two days later, the cells are transferred into medium containing neither serum nor antibiotics and are incubated with 2 µg/ml plasmid pSV7d containing the cDNA of flt-1 or of flk-1 (donated by L. Williams, UCSF) and 10 µg/ml lipofectin for 30 minutes.

After 6 hours, the medium is replaced by DMEM containing 10% foetal calf serum for 48 hours.

The binding of radioiodinated VEGF ($1-2\times10^5$ cpm/ng) to the transfected COS cells is measured at 4° C. The cells are washed twice with binding buffer (DMEM containing 20 mM Hepes and 1 mg/ml gelatine adjusted to a pH of 7.4). The desired concentrations of iodinated VEGF (1 ng/ml for the COS/flt-1 cells and 10 ng/ml for the COS/flk-1 cells) are added with various concentration of non-labelled VEGF or Ig2 Id or Ig2 J under a final volume of 0.5 ml. The non-specific binding is determined in the presence of an excess—500 ng—of purified VEGF. The total and non-specific binding is determined in duplicate.

After two hours, the cells are washed 3 times with cold buffer and lysed with 0.5 ml 0.2 M NaOH. The iodine-125 contained in the solubilized material is counted in a gamma counter.

In parallel, FBAE cells (foetal bovine aortic endothelial cells) seeded at 100,000 cells per well of 10 cm² are cultured in DMEM medium containing 10% foetal calf serum and 100 IU/ml penicillin and 50 mg/ml streptomycin. 2 days later, the cells are transferred into medium containing neither serum nor antibiotics and are incubated with 10 mg/ml sense or antisense KDR oligonucleotides incubated beforehand with 10 mg/ml lipofectin for 30 minutes.

After 6 hours, the medium is replaced by DMEM containing 10% foetal calf serum for 24 hours. Non-transfected subconfluent FBAE cells are also incubated for 90 minutes with the anti-idiotypic IgG or the Ig1 PI. The cells are subsequently transferred to 4° C. and then incubated for 3 hours with various concentrations of iodinated VEGF in the presence (non-specific binding) or absence (total binding) of 1 µg/ml VEGF. The data are then analysed in accordance with the Scatchard plot (Scatchard, 1949) using the Munson program (Munson, 1980).

5. Biological Activities of the Antibodies

Phosphorylation of the Receptors

Figure 3:
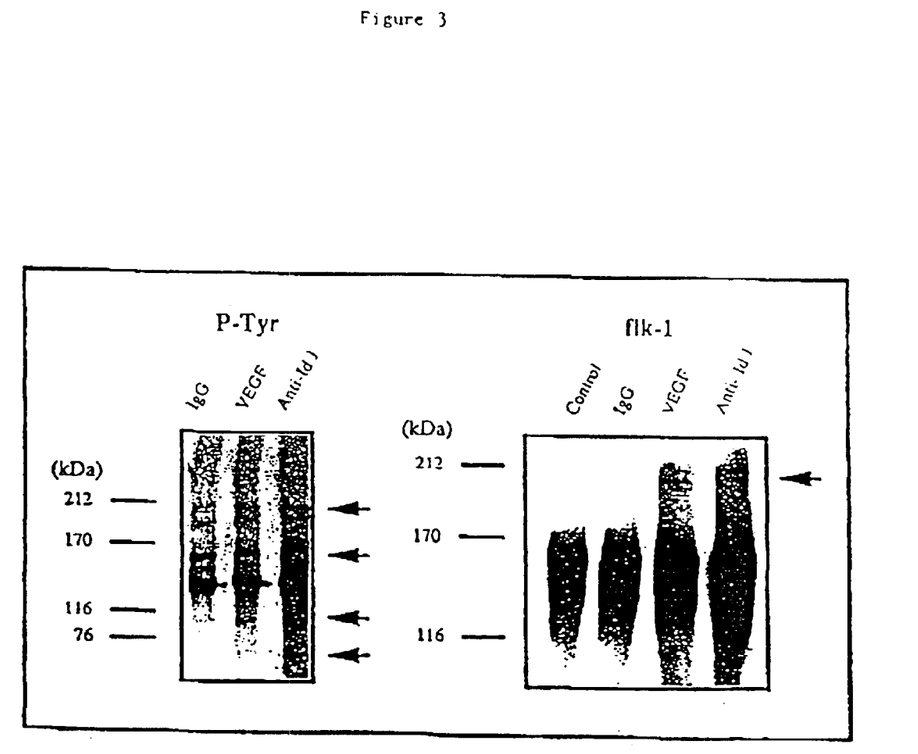
FIG. 3 shows the induction of phosphorylation by anti-idiotype J on the tyrosine residues of KDR/flk-1 in FBAE cells.

FBAE cells are stimulated for 10 min at 37° C. with 1 nM VEGF or Ig2 J and are then lysed in RIPA buffer (50 mM Tris, pH 7.5, 1% Nonidet P 40 Sigma, ref. N6507, 1 mM EDTA, 5 µg/ml of each of the following protease inhibitors: benzamidine, pepstatin, leupeptin and aprotinin), and the lysate is immunoprecipitated with an anti-phosphotyrosine monoclonal antibody (PY22, Amersham). The immunocomplexes are collected on protein A-sepharose beads and then separated by polyacrylamide gel electrophoresis. The proteins are transferred on to a nitrocellulose filter and revealed either by the anti-phosphotyrosine monoclonal antibody PY22 (FIG. 3) or by a commercial anti-flk-1 polyclonal antibody (Santa-Cruz) (FIG. 3).

Proliferation

FBAE cells seeded at 20,000 cells per well of 4 cm² are cultured in DMEM medium containing 10% foetal calf serum and 100 IU/ml penicillin and 50 µg/ml streptomycin. Two days later, the cells are transferred into medium containing neither serum nor antibiotics and are incubated with 10 µg/ml sense or antisense KDR oligonucleotides incubated beforehand with 10 µg/ml lipofectin for 30 minutes.

After 6 hours, the medium is replaced by DMEM containing 10% foetal calf serum. 24 hours later, the cells are transfected in medium without serum and then incubated in the presence of 50 pM VEGF, Ig2 J or PBS alone. Between the 68th and 72nd hour, 1 microcurie ($\mu$Ci) of tritiated thymidine is added. The cells are rinsed 3 times with PBS at 4° C. and once with trichloroacetic acid diluted to 10%, and then lysed in 0.2 M NaOH. The lysate is then counted with the aid of a scintillation counter.

In similar experiments, FBAE cells are seeded at 5,000 cells per well in plates of 12 wells in the presence of VEGF, Ig2 J or Ig1 PI at various concentrations ranging from 0.01 ng/ml to 1,000 ng/ml. After five days, the cells are trypsinized and counted. The data shown are the means of three points and the experiments were carried out four times with similar results.

Migration

ACE cells are seeded at 100,000 cells per well of 4 cm$^2$. The cells are removed from the monolayer over an area representing a Maltese cross with the aid of a cone of calibrated surface. The cells are rinsed and incubated with modulator (VEGF, Ig2 J, PBS) concentrations which are ten times higher than those used for the proliferation experiments. 24 hours later, the cells are stained with May-Grunwald-Giemsa stain and the cells which have migrated are counted over eight fields, each point being determined in triplicate. These experiments were carried out three times with similar results.

Corneal Angiogenesis

Lenticuli impregnated with 2 $\mu$l vehicle (PBS containing 50 mg bovine serum albumin) or vehicle and 200 ng VEGF or 600 ng Ig2 J are inserted into the corneal stroma at 2 mm from the limbus in New Zealand rabbits. After 12 days, the surface neovascularized with regard to the implant is quantified over a scale of 0 to 4 (Favard, 1992).

Tumour Angiogenesis

A prostate adenocarcinoma (Gleason grade IX) was propagated serially in immunodepressed mice (Iffa-Credo). One month later, the mice received an intraperitoneal injection of 200 $\mu$g Ig1 T or Ig1 PI or Ig2 Id (all the Ig purified by affinity for protein A-sepharose) twice a week. The tumours were measured twice a week. The mice were sacrificed 2 months later. The tumour sections were incubated with Mib-1 antibodies (Immunotech), which mark only the cells in the mitotic phase, ulex lectin (European) conjugated with peroxidase (Sigma), which marks only the endothelial cells, and anti-flt-1 antibody.

Results

Figure 1:
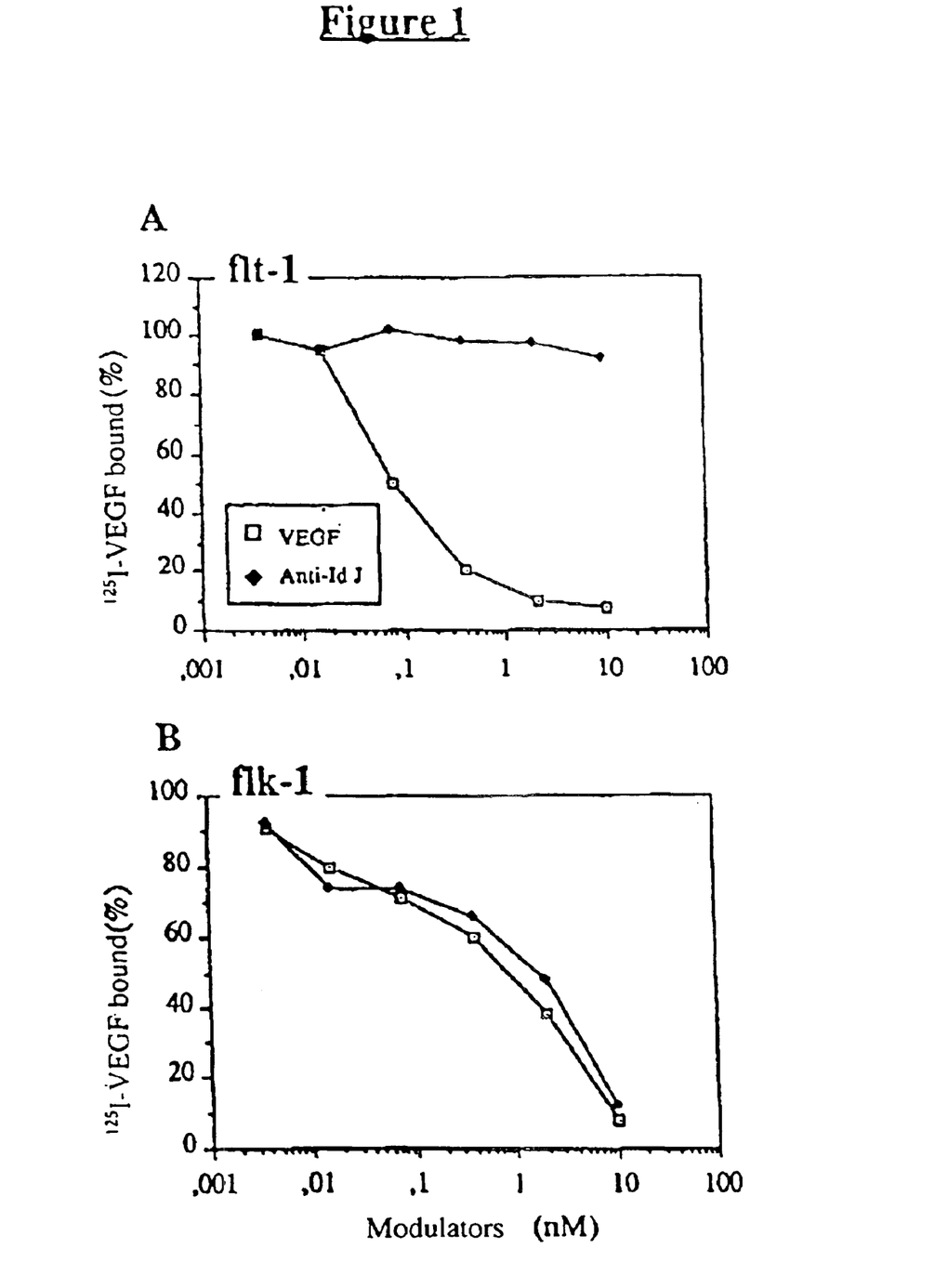
FIG. 1 shows the inhibition of the binding of iodinated VEGF to is receptors by the anti-idiotypic antibody J.

No pre-immune serum (n=18) contained IgG which interferes with the binding of iodinated VEGF on COS cells transfected by expression vectors of the flt-1 or fik-1 receptors. In contrast, 20% of the anti-idiotypic sera contain IgG which bind to flk-1. A preparation of Ig2 Id purified from serum collected between 4 and 7 months after the immunization was selected (Ig2 J), which totally inhibits binding of iodinated VEGF to COS cells transfected with flk-1 (the concentration which triggers off 50% inhibition is about 400 ng), but does not interfere with its binding to cells transfected by flt-1 (FIG. 1).

Figure 2A:
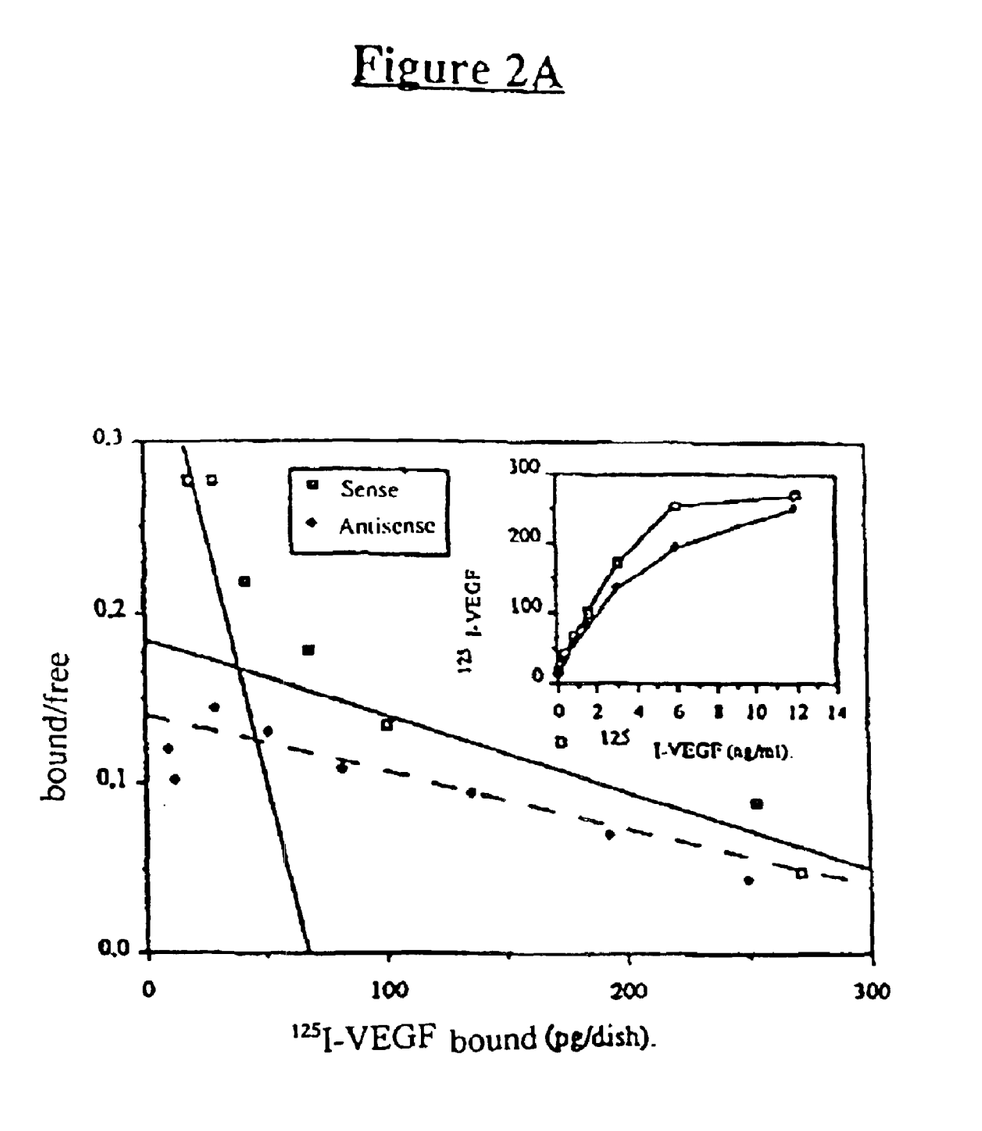
FIG. 2A shows the inhibition of the binding of VEGF to its receptor of high affinity by transfection of FBAE cells by antisense KDR oligonucleotides.
Figure 2B:
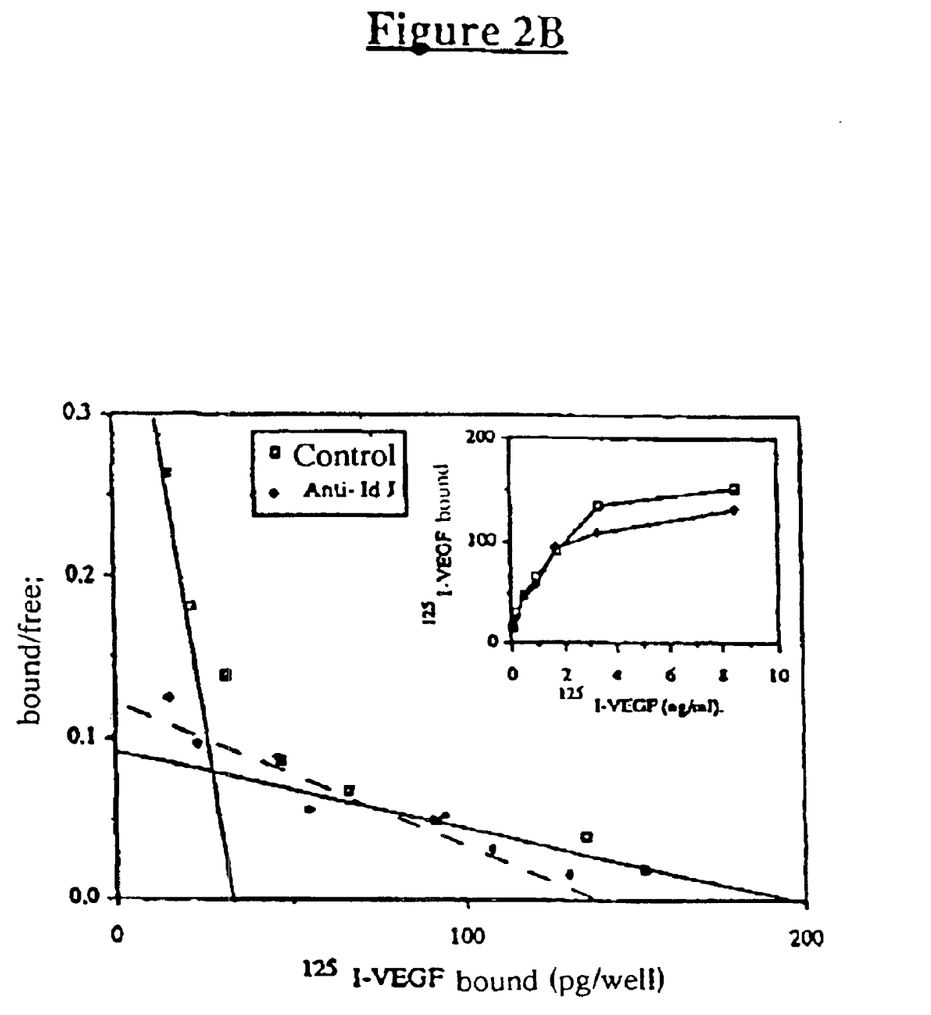
FIG. 2B shows the inhibition of the binding of VEGF to its receptor of high affinity on FBAE cells by pre-incubation with anti-idiotype J (anti-Id J).

Transfection of FBAE cells by antisense oligonucleotides of 15 mers centred on the codon for initiation of translation of KDR inhibits 20–25% of the binding sites of iodinated VEGF. Analysis of the results by a Scatchard plot has shown that this reduction in the binding was effected exclusively on the binding site of highest affinity 5 pM (FIG. 2A). Binding to this site is also inhibited by pre-incubation of FBAE cells with Ig2 J (FIG. 2B).

Ig2 J and VEGF induce phosphorylation on a tyrosine of a protein of 200 kDa. The revealing of this molecular species by antibodies directed against flk-1 confirms that the flk-1 receptor is readily phosphorylated by Ig2 J (FIG. 3).

Figure 4:
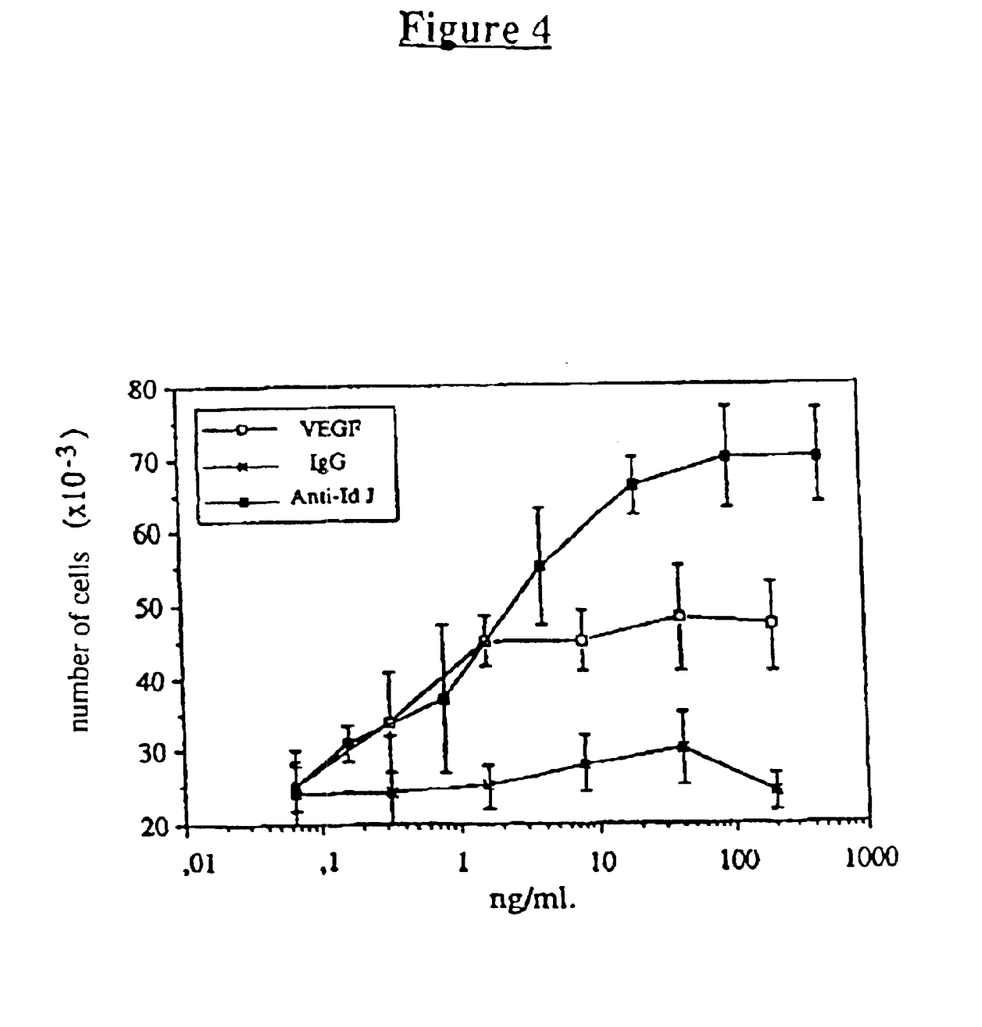
FIG. 4 shows the stimulation of the proliferation of FBAE cells by anti-idiotype J.

Ig2 J and VEGF induce the proliferation of ACE cells (half the maximum proliferation is obtained with 1.2 ng Ig2 J and 0.5 ng VEGF) at a level which is significantly greater than that obtained in the presence of VEGF, corresponding to 1.8 (VEGF) and 3.1 (Ig2 J) times the number of cells counted in the non-stimulated wells (FIG. 4).

In contrast, Ig2 J do not induce migration of endothelial cells (table 1).

In order to check whether these Ig modulate angiogenesis, implants containing 200 ng VEGF or 600 ng Ig2 J or PBS alone were grafted into the corneal stroma of rabbits. 12 days later, no neovascularization was observed with regard to the implants containing PBS alone. In contrast, a neovascularization of equivalent intensity was found with regard to implants containing 5 pmol VEGF or Ig2 J (2.78 and 2.45 respectively). Histological analysis of the retina showed no proliferative reaction, although VEGF is synthesized, at least in vitro, by endothelial cells, pericytes and pigmented epithelial cells.

Figure 5:
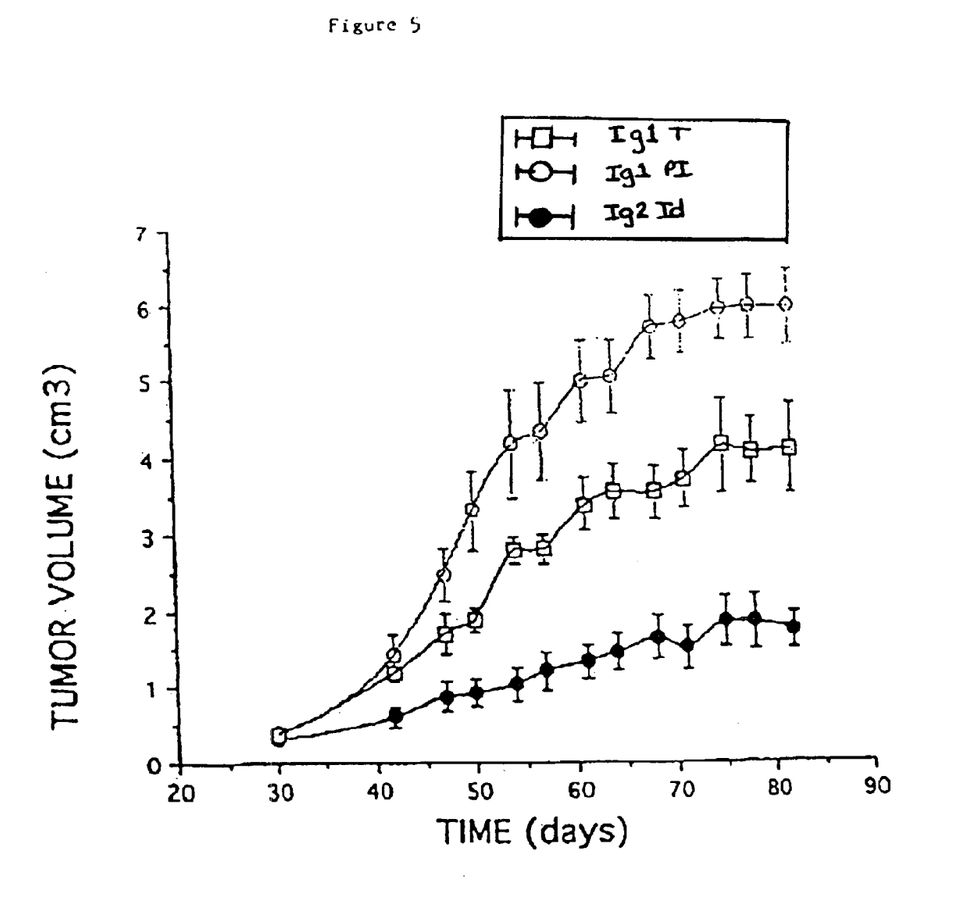
FIG. 5 shows the effects of injection of Ig2 Id on tumour volume.
Figure 6:
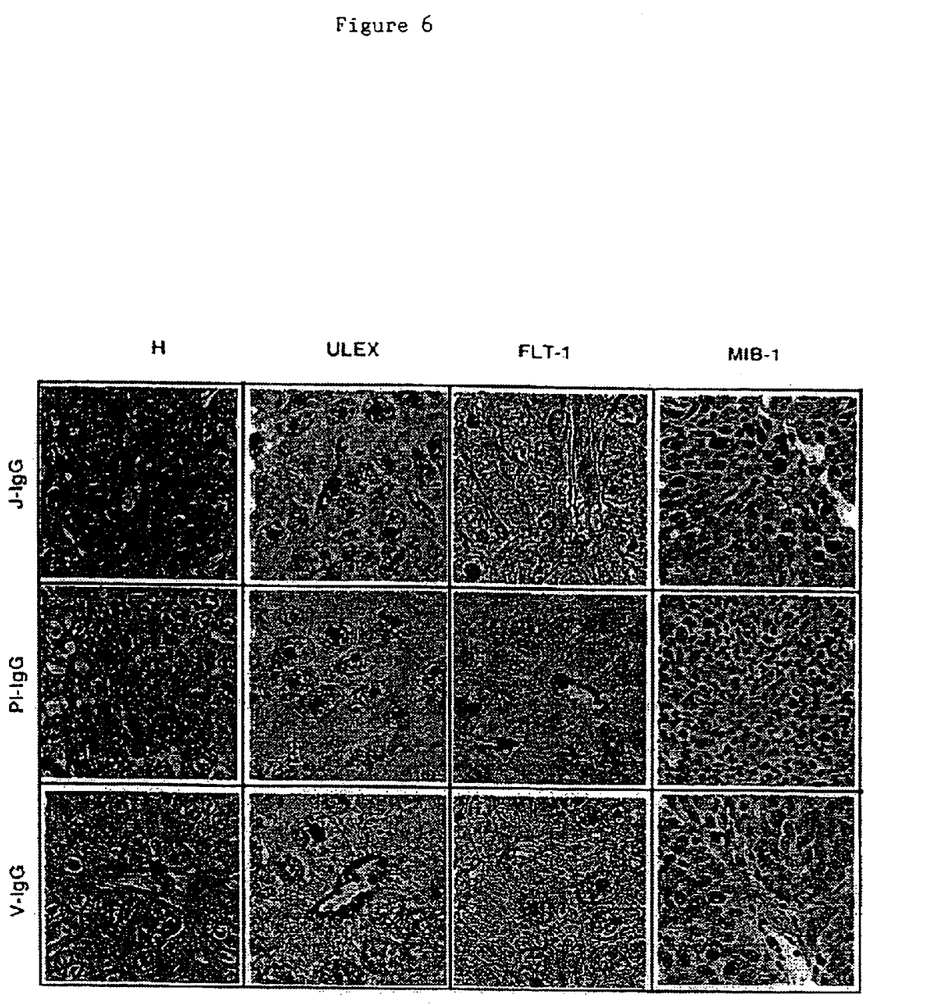
FIG. 6 shows the histological analysis (a–c), the marking of the vascularization (d–i) and the proliferation (j–l) of adenocarcinoma xenografts treated with V-IgG, PI-IgG or J-IgG.

Since VEGF is currently recognized as the major cause of tumour angiogenesis, these Ig2 Id were injected into mice into which fragments of prostate adenocarcinoma had been grafted one month previously. After 1 month of treatment with Ig2 J, the volume of the tumours is significantly greater than that of tumours treated with Ig1 PI (FIG. 5).

Immunohistochemical analysis of tumour section showed that these antibodies induce in vivo a cell proliferation measured by immunohistochemistry with the mib-1 antibody. In contrast, no positive cell . . . in the healthy organs (liver, kidney, lung, retina, brain), but stimulate angiogenesis, measured by the corneal implant test. These properties make it a specific marker of "activated" endothelial cells.

REFERENCES

Folkman J: How is blood vessel growth regulated in normal and neoplastic tissue. Cancer Res. 1986; 46:467–479.

Plouët J, Schilling J. Gospodarowicz D: Isolation and characterization of a newly identified endothelial cell mitogen produced by AtT20. EMBO J., 1989, 8, 3801–3806.

Ferrara N, Henzel W J: Pituitary follicular cells secrete a novel heparin binding growth factor specific for vascular endothelial cells. Biochem. Bioph. Res. Commun. 1989; 161:851–856.

Conn G, Soderman D D, Schaffer M T, Wile M, Hatcher V B, Thomas K A: Purification of a glycoprotein vascular endothelial cell mitogen from a rat glioma-derived cell line. Proc. Natl. Acad. Sci. 1990; 87:1323–1327.

Connolly D T, Olander J V, Heuvelman D, Nelson R, Monsell R. Siegel N, Haymore B L, Leimgruber R, Feder J: Human Vascular Permeability Factor. J. Biol. Chem, 1989; 264: 20017–20024.

Leung D W, Chachianes G, Kuang W J, Goeddel D W, Ferrara N: Vascular Endothelial Growth Factor is a secreted angiogenic mitogen. Science 1989; 246:1306–1309.

Keck P J, Hauser S D, Krivi G. Sanzo K, Warren T, Feder J, Connolly D T: Vascular Permeability Factor, an Endothelial Cell Mitogen Related to PDGF. Science 1989; 246: 1309–1312.

Tischer E, Gospodarowicz D, Mitchel R, Silva M, Schilling J, Lau K, Crisp T, Fiddes J C, Abraham J A: Vascular Endothelial Growth Factor: a new member of the Plateled-Derived Growth Factor Gene Family. Biochem. Bioph. Res. Commun. 1989; 165: 1198–1206.

De Vries C, Escobedo J, Ueno H, Houck K, Ferrara N, Lewis L T: The fms-like tyrosine kinase, a receptor for vascular endothelial growth factor. Science 1992; 255:989–991.

Terman B I, Vermazen M D, Carrion Me, Dimitrov D, Armellino D C, Gospodarowicz D, Bohlen P: Identification of the KDR tyrosine kinase as a receptor for vascular endothelial growth factor. Biochem. Biophys. Res. Commun. 1992; 34:1578–1586.

Millauer B, Wizigmann-Voos S, Schnurch H, Martinez R, Moller N P H, Risau W, Ullrich A: High affinity VEGF binding and developmental expression suggest Flk-1 as a major regulator of vasculogenesis and angiogenesis. Cell 1993; 72:835–846.

Quinn T P, Peters K G, Devries C, Ferrara N, Williams L T: Fetal liver kinase 1 is a receptor for vascular endothelial growth factor and is selectively expressed in vascular endothelium. Proc. Natl. Acad. Sci. 1993; 90:7533–7537.

Peters K G, DeVries C, Williams L T: Vascular endothelial growth factor receptor expression during embryogenesis and tissue repair suggests a role in endothelial differentiation and blood vessel growth. Proc. Natl. Acad. Sci. 1993; 90:8915–8919.

Kim K J, Li B, Winer J, Armanini M, Gilett N, Philips H S, Ferrara N: Inhibition of vascular endothelial growth factor-induced angiogenesis suppresses tumor growth in vivo. Nature 1993; 362:841–844.

Millauer B, Shawver L K, Plate K H, Risau W, Ullrich A, 1994. Glioblastoma growth inhibited in vivo by a dominant-negative flk-1 mutant. Nature; 367:576–579.

Folkman J, 1993. Diagnostic and therapeutic applications of angiogenesis research. C.R. Acad. Sci. Paris. 316:914–918.

Oberg C, Waltenberger J, Claesson-Welsh L, Welsh M, 1994.

Expression of protein tyrosine kinases in islet cells: possible role of the flk-1 receptor for b cell maturation from duct cells. Growth factors, 10:115–126.

Yamane A, Seetharam L, Yamaguchi S, Gotoh N, Takahashi T, Neufeld G, Shibuya M. A new communication system between hepatocytes and sinusoidal endothelial cells in liver through vascular endothelial growth factor and Flt tyrosine kinase receptor family (Flt-1 and KDR/Flk-1). Oncogene, 1994, 9:2683–2690.

Brooks P C, Montgomery A M P, Rosenfeld M, Reisfeld R A, Ku T, Klier G, Cheresh D A.

integrin avb3 antagonists promote tumor regression by inducing apoptosis of angiogenic blood vessels. Cell, 1994, 79:1157–1164.

We claim:

1. Anti-idiotypic vascular endothelial growth factor antibody, said antibody being a ligand of the human KDR receptor or of the murine flk-1 receptor and not a ligand of flt.

2. Anti-idiotypic vascular endothelial growth factory antibody, having the following properties:
   a) it targets angiogenic endothelial cells,
   b) it is circulating,
   c) it has a half-life of about 23 days,
   d) it induces phosphorylation on a tyrosine of a protein of 200 kDa,
   e) it induces proliferation of vascular endothelial cells,
   f) it does not induce migration of endothelial cells,
   g) it stimulates angiogenesis,
   h) it does not cause arterial hypotension, and
   i) it does not affect the permeability of vessels.

3. Fab fragment of the anti-idiotypic antibody according to claim 1.

4. Fab fragment of the anti-idiotypic antibody according to claim 2.

5. Complex between an anti-idiotypic antibody according to claim 1 and a toxin, or between an anti-idiotypic antibody according to claim 1 and a radioactive element.

6. Anti-idiotypic antibody according to claim 1 produced by the following steps:
   a) purified VEGF is injected into an animal,
   b) blood is withdrawn to recover purified Ig containing specific anti-VEGF IgG, and then in an optional stage the specific anti-VEGF IgG are purified from the purified Ig,
   c) said purified Ig or said purified anti-VEGF IgG are injected into an animal of the same origin as that used for injection of the VEGF,
   d) blood is withdrawn to recover the total Ig, and then to subject the total Ig to two immunoadsorptions:
      (i) an immunoadsorption on an affinity column prepared with the pre-immune Ig of the animal which has been used to produce the anti-VEGF IgG, to eliminate the anti-allotypic or isotypic antibodies,
      (ii) an immunoadsorption on an affinity column prepared with the anti-VEGF IgG, to purify the anti-idiotypes.

7. Pharmaceutical composition, comprising an anti-idiotypic antibody according to claim 1.

8. Pharmaceutical composition, comprising an anti-idiotypic antibody according to claim 2.

9. Pharmaceutical composition, comprising the Fab fragment according to claim 3.

10. Pharmaceutical composition, comprising the complex according to claim 5.

* * * * *